United States Patent [19]

Rao et al.

[11] Patent Number: 5,945,589
[45] Date of Patent: Aug. 31, 1999

[54] DERIVATIVES OF *BAUHINIA PURPUREA* LECTIN AND THEIR USE AS LARVICIDES

[75] Inventors: A. Gururaj Rao, Urbandale; Nandha Kumar Balasubramaniam, Des Moines, both of Iowa

[73] Assignee: Pioneer Hi-Bred International, Inc., Des Moines, Iowa

[21] Appl. No.: 08/038,761

[22] Filed: Mar. 24, 1993

Related U.S. Application Data

[63] Continuation-in-part of application No. 07/921,179, Jul. 24, 1992.
[51] Int. Cl.[6] ............................ A01H 5/00; C12N 15/82; C12N 5/04
[52] U.S. Cl. ................... 800/320.1; 800/301; 435/419; 435/320.1; 435/252.3; 514/2; 530/370
[58] Field of Search ...................... 800/205, 279, 800/298, 301, 320.1; 435/172.3, 240.4, 320.1, 67, 418, 419, 440, 468, 472, 252.3; 530/350, 370; 71/1; 514/2

[56] References Cited

PUBLICATIONS

Kusui et al (Jun. 1991), J. Biochem 109: 899–903.

Kunkel (1985) Proc. Natl. Acad. Sci USA 82: 488–492.

Pratt et al (1990) Plant Physiol 93 : 1453–1459.

Fischhoff et al (1987) Bio/Technology 5 : 807–813.

Fromm et al (1990) Bio/Technology 8: 833–839.

*Primary Examiner*—Elizabeth F. McElwain

[57] ABSTRACT

Compounds which are derived from *Bauhinia purpurea* lectin by replacement of one or more lysine residues in the molecule with other amino acid residues which either preserve the positive charge at the position of the substitution or provide a neutral residue at the position of the substitution are effective larvicides against insects such as European corn borer.

20 Claims, No Drawings

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 262 residues
      (B) TYPE: amino acid
      (C) STRANDEDNESS: single
      (D) TOPOLOGY: linear (ii) MOLECULE TYPE: protein
      (A) DESCRIPTION:

(iii) HYPOTHETICAL: No (iv) ANTI-SENSE: NO (v) FRAGMENT TYPE:

(vi) ORIGINAL SOURCE:
      (A) ORGANISM: Bauhinea purpurea
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

```
    (vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO: 1:

Thr Ser Ser Thr Leu Thr Gly Phe Thr Phe Pro Asn Phe Trp Ser
 1               5                  10                  15

Asn Thr Gln Glu Asn Gly Thr Glu Ile Ile Phe Leu Gly Asn Ala
                20                  25                  30

Thr Tyr Thr Pro Gly Ala Leu Arg Leu Thr Arg Ile Gly Glu Asp
                35                  40                  45

Gly Ile Pro Leu Lys Ser Asn Ala Gly Gln Ala Ser Tyr Ser Arg
                50                  55                  60

Pro Val Phe Leu Trp Asp Ser Thr Gly His Val Ala Ser Phe Tyr
                65                  70                  75

Thr Ser Phe Ser Phe Ile Val Arg Ser Ile Asp Val Pro His Ile
                80                  85                  90

Thr Ala Asp Gly Phe Ala Phe Phe Leu Ala Pro Val Asp Ser Ser
                95                  100                 105

Val Lys Asp Tyr Gly Gly Cys Leu Gly Leu Phe Arg Tyr Lys Thr
                110                 115                 120

Ala Thr Asp Pro Ser Lys Asn Gln Val Val Ala Val Glu Phe Asp
                125                 130                 135

Thr Trp Pro Asn Thr Glu Trp Ser Asp Leu Arg Tyr Pro His Ile
                140                 145                 150

Gly Ile Asn Val Asn Ser Thr Val Ser Val Ala Thr Thr Arg Trp
                155                 160                 165

Asp Asn Asp Asp Ala Tyr Val Thr Lys Ser Thr Ala His Ile Thr
                170                 175                 180

Tyr Asp Ala Thr Ser Lys Ile Ile Thr Val Leu Leu Thr Tyr Asp
                185                 190                 195

Asn Gly Arg His Tyr Gln Leu Ser His Val Val Asp Leu Pro Lys
                200                 205                 210

Ile Leu Pro Glu Arg Val Arg Ile Gly Phe Ser Gly Gly Thr Gly
                215                 220                 225

Phe Asn Glu Thr Gln Tyr Ile Leu Ser Trp Ser Phe Thr Ser Thr
```

```
                    230              235              240
Leu Asn Ser Thr Lys Ile Ser Ala Leu Thr Gln Lys Leu Arg Ser
                245              250              255
Ser Ala Ser Tyr Ser Ser Met
                260
```

DERIVATIVES OF *BAUHINIA PURPUREA* LECTIN AND THEIR USE AS LARVICIDES

CROSS-REFERENCE TO COPENDING APPLICATION

This is a continuation-in-part of prior copending U.S. patent application Ser. No. 07/921,179, filed Jul. 24, 1992.

TECHNICAL FIELD

This invention relates to materials and methods for killing insect larvae which are harmful to plants, and materials and methods for imparting insect resistance to plants, material harvested from the plants, and products derived from the harvested material.

BACKGROUND OF THE INVENTION

Numerous insects are serious pests of common agricultural crops. One method of controlling insects has been to apply insecticidal organic or semiorganic chemicals to crops. This method has numerous, art-recognized problems. A more recent method of control of insect pests has been the use of biological control organisms which are typically natural predators of the troublesome insects. These include other insects, fungi (milky-spore) and bacteria (*Bacillus thuringiensis* cv., commonly referred to as "Bt"). However, it is difficult to apply biological control organisms to large areas, and even more difficult to cause those living organisms to remain in the treated area for an extended period. Still more recently, techniques in recombinant DNA have provided the opportunity to insert into plant cells cloned genes which express insecticidal toxins derived from biological control organisms such as Bt. This technology has given rise to additional concerns about eventual insect resistance to well-known, naturally occurring insect toxins, particularly in the face of heavy selection pressure, which may occur in some areas. Thus, a continuing need exists to identify naturally occurring insecticidal toxins which can be formed by plant cells directly by translation of a structural gene.

The lectin from *Bauhinia purpurea* is a glycoprotein the cDNA-derived amino acid sequence of which indicates a polypeptide chain comprising 262 amino acids that include 7 lysine residues. See, e.g., "cDNA Cloning and Expression of *Bauhinia purpurea* Lectin," Kusui et al., *J. Biochem.* 109, 899–903 (1991). This lectin has been determined by Czapla et al. to have larvicidal activity against European corn borer, as disclosed in the copending, commonly assigned U.S. patent application "Larvicidal Lectins and Plant Insect Resistance Based Thereon," filed Sep. 20, 1991, Ser. No. 07/763,100. One of us is also a coinventor of that application. Other insects show little susceptibility to this lectin, and acquired resistance to naturally occurring lectins is likely to exist. Thus, a continuing need is felt for new larvicidal proteins which are not found in nature, yet can easily be expressed in plant cells as a gene product of a single structural gene.

DISCLOSURE OF THE INVENTION

It has now been discovered that the lysine residues in *Bauhinia purpurea* lectin (BPL) can be guanidinated (retaining positive charge) or carbamylated (conversion to a neutral residue) without changing the larvicidal activity of the compound. Likewise, the compound can be deglycosylated, either in its native or its denatured form, without loss of larvicidal activity. Biochemical properties such as hemagglutination and ability to bind N-acetylgalactosamine are also unchanged. However, modification of the lysine residues by succinylation (conversion to negative charge) abolishes the larvicidal activity of the lectin and also its ability to bind GalNAc. Thus, it has been determined that amino acid substitutions at the lysine residues which either conserve the positive charge or convert the position to a neutral residue can be performed without loss of insecticidal activity, but substitutions which replace lysine residues with residues which carry a negative charge cannot be introduced into the molecule and still retain larvicidal activity.

Accordingly, the present invention provides larvicidal compounds having the non-lysine amino acid sequence of *Bauhinia purpurea* lectin but having one or more of the lysine residues in the sequence replaced by an amino acid residue selected from Ala, Arg, Asn, Gln, Gly, His, Ile, Leu, Met, Phe, Ser, Thr, Trp, Tyr, or Val. The same substitution need not be made at each lysine residue. That is, within the scope and context of this invention one lysine may be replaced by methionine and another by threonine to produce a larvicidal protein compound based on, but different from, BPL. These compounds are proteins which can be expressed as the gene product of single structural genes. Such genes can be synthesized by known methods, or readily prepared from the native BPL structural gene by site-directed mutagenesis, another well characterized technique for gene modification.

The larvicidal compounds of this invention can be effectively applied to plants, harvested plant materials, or products consumed by the larvae by spray, dust or other formulation common to the insecticidal arts. By "harvested plant material" herein is meant any material harvested from an agricultural or horticultural crop, including without limitation grain, fruit, leaves, fibers, seeds, or other plant parts. Products derived or obtained from such harvested material include flour, meal, and flakes derived from grain, and products in which such materials are admixed, such as, for example, cake, cookie, pancake and biscuit mixes. Alternatively, the larvicidal compound can be incorporated into the tissues of a susceptible plant so that in the course of infesting the plant, its harvested material, or a product derived from the harvested plant material, the larvae consume larvicidal amounts of the compound. One method of doing this is to incorporate the compound in a non-phytotoxic vehicle which is adapted for systemic administration to the susceptible plants. This method is commonly employed with insecticidal materials which are designed to attack chewing insects and is well within the purview of one of ordinary skill in the art of insecticide and larvicide formulation. However, since genes which code for these compounds can also be synthesized, either directly using a DNA sequence obtained by working backwards from the known amino acid sequence and preferably using plant-preferred codons, or by site directed mutagenesis of the gene which codes for native BPL, the resulting sequence can be inserted into an appropriate expression cassette, and introduced into cells of a susceptible plant species or a suitable endophytic bacterium, so that an especially preferred embodiment of this method involves inserting into the genome of the plant or bacterium a DNA sequence coding for one or more insecticidal compounds according to this invention, in proper reading frame relative to transcription initiator and promoter sequences active in the plant or bacterium. Transcription and translation of the DNA sequence under control of the regulatory sequences causes expression of the larvicidal gene product at levels which provide an insecticidal amount of the compound in the tissues of the plant which are normally infested by the larvae. Alternatively, a dietary bait containing one or more of the selected compounds can be employed, with, optionally, an added pheromonal or other larval attractant material.

The plant is preferably a plant susceptible, or whose harvested material or products are susceptible to infestation and damage by the larvae of one or more insect larvae such as European corn borer, or whose harvested material is subject to attack by larvae of such insects. These include corn (*Zea mays*), wheat (*Triticum aestivum*) and sorghum (*Sorghum bicolor*). However, this is not to be construed as limiting, inasmuch as these species have in the past been among the most difficult commercial crops to reliably transform and regenerate, and these insects (under other common names) also infest certain other crops. Thus the methods of this invention are readily applicable via conventional techniques to numerous plant species, if they are found to be susceptible to the plant pests listed hereinabove, including, without limitation, species from the genera *Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Triticum*, and *Datura*.

Preferred plants that are to be transformed according to the methods of this invention are cereal crops, including maize, rye, barley, wheat, sorghum, oats, millet, rice, triticale, sunflower, alfalfa, rapeseed and soybean, fiber crops, such as cotton, fruit crops, such as melons, and vegetable crops, including onion, pepper, tomato, cucumber, squash, carrot, crucifer (cabbage, broccoli, cauliflower), eggplant, spinach, potato and lettuce.

The DNA sequence which when expressed imparts insecticidal activity is a structural gene which codes for a BPL derivative compound according to this invention. It has been found that these compounds have sufficient insecticidal (larvicidal) activity to be operative in a plant cell expression system. That is, while certain other proteins have some larvicidal activity at high concentrations in pure form, plant cell expression at such high concentrations is either not possible in a living plant cell system, or is not feasible if the commercially useful characteristics of the plant are to be preserved in terms of production of oils, starches, fibers, or other materials.

A tissue specific promoter can be used in any instance where it may be desirable to localize production of the compound to an infested tissue or to a tissue which is efficient in production of the larvicidal compound.

In carrying out this invention, it will be appreciated that numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong constitutive promoter sequence at one end to cause the gene to be transcribed at a high frequency, and a poly-A recognition sequence at the other end for proper processing and transport of the messenger RNA. An example of such a preferred (empty) expression cassette into which the DNA sequence of the present invention can be inserted is the pPHI414 plasmid developed by Beach et al. of Pioneer Hi-Bred International, Inc., Johnston, Iowa. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as selectable markers to identify and separate transformed cells. Preferred selection agents include kanamycin, chlorosulfuron, phosphonothricin, hygromycin and methotrexate, and preferred markers are genes conferring resistance to these compounds. A cell in which the foreign genetic material in a vector is functionally expressed has been "transformed" by the vector and is referred to as a "transformant".

A particularly preferred vector is a plasmid, by which is meant a circular double-stranded DNA molecule that is not a part of the chromosomes of the cell.

As mentioned above, genomic, synthetic and cDNA encoding the gene of interest may be used in this invention. The vector of interest may also be constructed partially from a cDNA clone, partially from a synthetic sequence and partially from a genomic clone. When the gene sequence of interest is in hand, genetic constructs are made which contain the necessary regulatory sequences to provide for efficient expression of the gene in the host cell. According to this invention, the genetic construct will contain (a) a first genetic sequence coding for the larvicidal compound of interest and (b) one or more regulatory sequences operably linked on either side of the structural gene of interest. Typically, the regulatory sequences will be selected from the group comprising of promoters and terminators. The regulatory sequences may be from autologous or heterologous sources.

Promoters that may be used in the genetic sequence include nos, ocs, phaseolin, CaMV, FMV and other promoters isolated from plants or plant pests.

An efficient plant promoter that may be used is an overproducing plant promoter. Overproducing plant promoters that may be used in this invention include the promoter of the small sub-unit (ss) of the ribulose-1,5-biphosphate carboxylase from soybean (Berry-Lowe et al, *J. Molecular and App. Gen.*, 1:483–498 (1982)), and the promoter of the cholorophyll a-b binding protein. These two promoters are known to be light-induced, in eukaryotic plant cells (see, for example, *Genetic Engineering of Plants, An Agricultural Perspective*, A. Cashmore, Pelham, N.Y., 1983, pp. 29–38, G. Coruzzi et al., *J. Biol. Chem.*, 258:1399 (1983), and P. Dunsmuir, et al., *J. Molecular and App. Gen.*, 2:285 (1983)).

The expression cassette comprising the structural gene for the compound of interest operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. typhimurium*, and *S. marcescens*. Eukaryotic hosts such as yeast or filamentous fungi may also be used in this invention.

The isolated cloning vector will then be introduced into the plant cell using any convenient technique, including electroporation (in protoplasts), retroviruses, microparticle bombardment, and microinjection, into cells from monocotyledonous or dicotyledonous plants, in cell or tissue culture, to provide transformed plant cells containing as foreign DNA at least one copy of the DNA sequence of the plant expression cassette. Preferably, the monocotyledonous species will be selected from maize, sorghum, wheat and rice, and the dicotyledonous species will be selected from soybean, sunflower, cotton, rapeseed (either edible or industrial), alfalfa, tobacco, and Solanaceae such as potato and tomato. Using known techniques, protoplasts can be regenerated and cell or tissue culture can be regenerated to form whole fertile plants which carry and express the desired gene for the selected protein. Accordingly, a highly preferred embodiment of the present invention is a transformed maize plant, the cells of which contain as foreign DNA at least one copy of the DNA sequence of an expression cassette of this invention.

This invention also provides methods of imparting resistance to insects such as European corn borer to plants of a susceptible taxon, comprising the steps of:

a) culturing cells or tissues from at least one plant from the taxon, b) introducing into the cells of the cell or tissue culture at least one copy of an expression cassette comprising a structural gene coding for a larvicidal compound according to this invention, or a combination of such compounds, operably linked to plant regulatory sequences which cause the expression of the structural gene in the cells, and c) regenerating insect-resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the protein structural gene and associated regulatory sequences via crossing and backcrossing. Such intermediate methods will comprise the further steps of a) sexually crossing the insect-resistant plant with a plant from the insect-susceptible taxon;

b) recovering reproductive material from the progeny of the cross; and c) growing insect-resistant plants from the reproductive material. Where desirable or necessary, the agronomic characteristics of the susceptible taxon can be substantially preserved by expanding this method to include the further steps of repetitively:

a) backcrossing the insect-resistant progeny with insect-susceptible plants from the susceptible taxon; and b) selecting for expression of insect resistance (or an associated marker gene) among the progeny of the backcross, until the desired percentage of the characteristics of the susceptible taxon are present in the progeny along with the gene imparting insect resistance.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into *Agrobacterium tumefaciens*, which can then be used to transfer the vector into susceptible plant cells, primarily from dicotyledonous species. Thus, this invention provides a method for imparting insect resistance in *Agrobacterium tumefaciens*-susceptible dicotyledonous plants in which the expression cassette is introduced into the cells by infecting the cells with *Agrobacterium tumefaciens*, a plasmid of which has been modified to include a plant expression cassette of this invention.

Finally, insect pests of harvested material, including stored grain, can also be targets for the compositions and methods of this invention. In view of this, the invention also provides a methods and compositions for killing larvae of susceptible insect pests of harvested materials and products obtained from harvested materials, comprising applying to the grain or causing to be expressed in the grain a larvicidal compound of this invention.

The following description further exemplifies the compositions of this invention and the methods of making and using them. However, it will be understood that other methods, known by those of ordinary skill in the art to be equivalent, can also be employed.

EXAMPLE 1

Succinylation of the Native Lectin

The purified lectin from Bauhinia purpurea was obtained from vector Laboratories. O-methylisourea and succinic anhydride were purchased from Sigma Chemical Co. Potassium cyanate was purchased from Aldrich Chemical Co.

Succinylation was performed according to known methods, in particular, the method published by Klotz, I. M. (1967) *Methods in Enzymology*, Vol. 11, pp. 576–580: To every mole of ϵ-amino group was added 100 moles of succinic anhydride. The addition was carried out in small aliquots with constant stirring over a period of 1–2 hours at room temperature. The pH of the mixture was maintained at between 8.0 and 8.5 by adding 5 M NaOH. After the addition of succinic anhydride the protein solution was allowed to react at room temperature for 30 to 60 minutes. The succinylated protein was then exhaustively dialyzed against PBS at a pH of 7.4 to remove the excess reagent.

The extent of succinylation was determined by the trinitrobenzenesulfonic acid (TNBS) method of Hall, R. J., Trinder, N. and Girens, D. I. (1973), *Analyst* 98, 673–686: 0.25 mg of the native and modified lectin were solubilized in 0.3 ml of 4% sodium carbonate. For the blank, 0.875 ml if 12 N HCl was added prior to the addition of TNBS. 0.25 μl of 1.25% TNBS in water was then added to all tubes. The samples were then allowed to react at 41° C. for 2 hours. After incubation the reaction was stopped by addition of 0.875 ml of 12 N HCl to all tubes except the blank. The tubes were then incubated at 105° C. for 3 hours, cooled to room temperature, and the the final volume was made up to 2 ml with water. All the samples were then extracted twice with diethyl ether, following which the residual ether was removed by evaporation. The absorbance of the samples was then measured at 415 nm. By taking the untreated protein as 100, the extent of succinylation was determined. There was a decrease in the absorbance at 415 nm with an increase in succinylation.

EXAMPLE 2

Carbamylation of the Native Lectin

Carbamylation (conversion to neutral residue) was performed according to known methods, in particular, the published method of Stark, G. R. (1972) *Methods in Enzymology*, Vol. 25, pp. 579–584: To every mole of the lectin in PBS at pH 8.0 was added 400 moles of potassium cyanate and the resulting mixture was allowed to react at room temperature for 48 hours. Unreacted reagents were removed by extensive dialysis against PBS at a ph of 7.4.

EXAMPLE 3

Guanidination of the Native Lectin

Guanidination (with retention of positive charge) was performed according to known methods, in particular the published method of Condrea, E., Rapuano, B. E., Fletcher, J. E., Yang, C. C., and Rosenberg, P. (1983), *Toxicon* 21, pp. 209–218: The lectin was treated with 0.5 M O-methylisourea at pH 10.8 and the mixture was allowed to react at 4° C. for 72 hours. Excess reagents were removed by dialysis against PBS at a pH of 7.4.

The extent of carbamylation and guanidination were determined by amino acid analysis, as homoarginine and homocitrulline respectively.

EXAMPLE 4

Larvicide Bioassays

Neonate larvae of O. nubilalis were reared according to standard protocols, such as those published by Czapla and Lang, *J. Economic Entomology* 83, 2480–2485 (1990). They were used in a bioassay in which the test compound at a concentration of 2.5 mg/ml was applied as a topical solution to the diet on which the larvae were fed. Plastic trays were used, with one larva per cell. Each cell contained 1.2 to 1.3 g of Stoneville artificial media at a pH of 5.6. The lectins were applied in PBS solutions in amounts of 100 μl per cell. PBS alone served as a negative control. Eight insects were used per treatment and the experiment was repeated on two consecutive days. weight and mortality of the insects was recorded at 7 days.

Native, carbamylated and guanidinated lectins caused 100% mortality when fed to the neonate larvae. Neonate larvae fed succinylated lectin survived and had weights comparable to those treated with the PBS control. Statistical analysis of the raw data showed that the difference was significant at the 95% level.

EXAMPLE 5

Modification of Lysine Residues

Sequence analysis performed by us indicated the presence of 9 lysine residues and an overall sequence in agreement with that already published by Kusui et al., *J. Biochem.* 109, 899–903 (1991). The sequence is as follows:

$NH_3$-Ser-Ser-Thr-Leu-Thr-Gly-Phe-Thr-Phe-Pro-Asn-Phe-Trp-Ser-Asn-Thr-Gln-Glu-Asn-Gly-Thr-Glu-Ile-Ile-Phe-Leu-Gly-Asn-Ala-Thr-Tyr-Thr-Pro-Gly-Ala-Leu-Arg-Leu-Thr-Arg-Ile-Gly-Glu-Asp-Gly-Ile-Pro-Leu-<u>Lys</u>-Ser-Asn-Ala-Gly-Gln-Ala-Ser-Tyr-Ser-Arg-Pro-Val-Phe-Leu-Trp-Asp-Ser-Thr-Gly-His-Val-Ala-Ser-Phe-Tyr-Thr-Ser-Phe-Ser-Phe-Ile-Val-Arg-Ser-Ile-Asp-Val-Pro-His-Ile-Thr-Ala-Asp-Gly-Phe-Ala-Phe-Phe-Leu-Ala-Pro-Val-Asp-Ser-Ser-Val-<u>Lys</u>-Asp-Tyr-Gly-Gly-Cys-Leu-Gly-Leu-Phe-Arg-Tyr-<u>Lys</u>-Thr-Ala-Thr-Asp-Pro-Ser-<u>Lys</u>-Asn-Gln-Val-Val-Ala-Val-Glu-Phe-Asp-Thr-Trp-Pro-Asn-Thr-Glu-Trp-Ser-Asp-Leu-Arg-Tyr-Pro-His-Ile-Gly-Ile-Asn-Val-Asn-Ser-Thr-Val-Ser-Val-Ala-Thr-Thr-Arg-Trp-Asp-Asn-Asp-Asp-Ala-Tyr-Val-Thr-<u>Lys</u>-Ser-Thr-Ala-His-Ile-Thr-Tyr-Asp-Ala-Thr-Ser-<u>Lys</u>-Ile-Ile-Thr-Val-Leu-Leu-Thr-Tyr-Asp-Asn-Gly-Arg-His-Tyr-Gln-Leu-Ser-His-Val-Val-Asp-Leu-Pro-<u>Lys</u>-Ile-Leu-Pro-Glu-Arg-Val-Arg-Ile-Gly-Phe-Ser-Gly-Gly-Thr-Gly-Phe-Asn-Glu-Thr-Gln-Tyr-Ile-Leu-Ser-Trp-Ser-Phe-Thr-Ser-Thr-Leu-Asn-COOH. The lysine residues in this sequence are highlighted for reference. This sequence corresponds to that indicated in Sequence ID No. 1.

EXAMPLE 6

Deglycosylation of *Bauhinea purpurea* lectin

Enzymatic deglycosylation of BPL under both native and denaturing conditions was performed by digestion with the endo-glycosidase Peptide-N-Glycosidase F, (Boehringer-Mannheim, Indianapolis, Ind.) for 18 hrs. at 37° C., with other conditions as described in the reagent kit. Denatured BPL was obtained by heating 1 ml of 5 mg/ml protein in 0.1% SDS at 100° C. for 2 minutes. After cooling to room temperature, n-octylglucoside (0.5%) and EDTA (50 mM) were added, boiled for 2 more minutes and returned to room temperature. The solution was then diluted to 2 ml with PBS pH 7.4 and subsequently treated with the enzyme. Following deglycosylation, the samples were exhaustively dialyzed against 0.1 M ammonium bicarbonate, lyophilized and analyzed on a 10–30% SDS-acrylamide gradient gel as described by Laemmli, U. K., *Nature,* 227, 680–5 (1970)

EXAMPLE 7

Toxicity of Deglycosylated BPL to European Corn Borer

Neonate larvae of O. nubilalis were reared as previously described by Czapla and Lang, supra. They were used in a topical bioassay essentially as described by Czapla and Lang but modified as described by Balasubramaniam, N. K., Czapla, T. H., and Rao, A. G., *Arch. Biochem. Biophys.,* 288:374–9 (1991).

BPL and modified BPL were prepared as 2.5 mg/ml solutions in PBS and a 100 μl aliquot of each protein was used per cell containing one larva. PBS served as the control treatment. Eight insects were used per treatment and it was repeated on two consecutive days. Weight and mortality were recorded after 7 days. The effect of modified BPA on larval weight was evaluated using a one-way treatment design, where all five treatments were replicated in a randomized complete block. The recommendations of Milliken, G. and Johnson, D., *The Analysis of Messy Data,* p. 31 (Van Nostrand Reinhold Co., New York, N.Y. 1984) for multiple range tests were employed for making comparisons among the treatment averages. Results were as indicated in Table 1.

TABLE 1

Effects of BPL and Modified BPL on Neonate ECB larvae after 7 Days

| Treatment | Weight + SEM[1] | Mortality (%)[2] |
|---|---|---|
| PBS | 6.6 + 2.7 | 0 |
| Control - BPL | — | 100 |
| Carb-BPL | — | 100 |
| Guan-BPL | — | 100 |
| Succ-BPL | 8.7 + 2.2 | 0 |
| Deglycosylated BPL (native) | — | 100 |
| Deglycosylated BPL (denatured) | — | 100 |
| Deglycosylation buffer | 4.2 + 1.1 | 0 |

[1]Weight is the average of live insects at 7 days from three replications ± standard error of the mean (SEM).
[2]Mortality is the number of dead insects for all replications divided by the total insects tested × 100 (n = 16).

---

What is claimed is:

1. A compound toxic to European corn borer and having the amino acid sequence of *Bauhinia purpurea* lectin except that one or more of the lysine residues is replaced by an amino acid selected from Ala, Arg, Asn, Gln, Gly, His, Ile, Leu, Met, Phe, Ser, Thr, Trp, Tyr, and Val.

2. A method of killing or inhibiting European corn borer larvae, comprising administering enterally to the larvae a larvicidal or feeding inhibitory amount of a compound according to claim 1.

3. A method according to claim 2 wherein the compound is administered enterally by incorporating the compound in the diet of the larvae.

4. A method according to claim 3 wherein the diet of the larvae comprises the tissues of a living plant.

5. A method for protecting a plant, harvested material from the plant, and products derived from the harvested material against infestation by European corn borer larvae comprising inserting into the genome of the plant at least one sequence coding for a peptide compound according to claim 1 or a combination of such compounds in proper reading frame relative to transcription initiator and promoter sequences active in the plant to cause expression of the sequence or sequences at levels which provide a larvicidal amount of the gene product in the tissues of the plant or harvested material of the plant which are normally infested by the larvae.

6. A method according to claim 5 wherein the plant is a monocotyledonous species selected from corn, wheat, rice, oats, rye, and sorghum.

7. A method according to claim 5 wherein the plant is a dicotyledonous species selected from soybean, sunflower, rapeseed, alfalfa, cotton, melon, cucumber, lettuce, pepper and tomato.

8. A DNA sequence which codes for a compound according to claim 1.

9. An expression cassette comprising a DNA sequence according to claim 8 operably linked to plant regulatory sequences which cause the expression of the DNA clone in plant cells.

10. An expression cassette comprising a DNA sequence according to claim 8 operably linked to bacterial expression regulatory sequences which cause the expression of the DNA clone in bacterial cells.

11. Bacterial cells containing as a foreign plasmid at least one copy of an expression cassette according to claim 10.

12. Transformed plant cells containing as foreign DNA at least one copy of the DNA sequence of an expression cassette according to claim 9.

13. Transformed cells according to claim 12, further characterized in being cells of a monocotyledonous species.

14. Transformed cells according to claim 13, further characterized in being maize, sorghum, wheat, oat, rye or rice cells.

15. Transformed cells according to claim 12, further characterized in being cells of a dicotyledonous species.

16. Transformed cells according to claim 15, further characterized in being soybean, alfalfa, sunflower, rapeseed, cotton, melon, cucumber, pepper, lettuce or tomato cells.

17. A transformed maize plant, the cells of which contain as foreign DNA at least one copy of the DNA sequence of an expression cassette according to claim 9.

18. A larvicidal composition, comprising a European corn borer larvicidal amount of a compound according to claim 1 or a combination of such compounds in a non phytotoxic vehicle.

19. A method of killing or controlling European corn borer larvae in harvested plant material, comprising applying to the harvested material a composition according to claim 18.

20. A method of killing or controlling European corn borer larvae in harvested plant material, comprising incorporating into the harvested materials a compound according to claim 1 or a combination thereof.

* * * * *